(12) United States Patent
Casasanta, Jr. et al.

(10) Patent No.: US 9,010,608 B2
(45) Date of Patent: Apr. 21, 2015

(54) RELEASABLE BUTTRESS RETENTION ON A SURGICAL STAPLER

(75) Inventors: Thomas Casasanta, Jr., Kensington, CT (US); Andrew Miesse, Durham, CT (US); Jennifer Whiffen, Meriden, CT (US); Elizabeth M. Contini, Hamden, CT (US); Sally Carter, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 654 days.

(21) Appl. No.: 13/325,404

(22) Filed: Dec. 14, 2011

(65) Prior Publication Data
US 2013/0153633 A1 Jun. 20, 2013

(51) Int. Cl.
*A61B 17/068* (2006.01)
*A61B 17/072* (2006.01)
*A61B 17/115* (2006.01)

(52) U.S. Cl.
CPC ....... *A61B 17/07292* (2013.01); *A61B 17/1155* (2013.01)

(58) Field of Classification Search
CPC .............................. A61B 17/068; A61B 17/115
USPC .................................. 227/176.1, 179.1, 175.1
See application file for complete search history.

(56) References Cited

U.S. PATENT DOCUMENTS

| 3,054,406 | A | 9/1962 | Usher |
|---|---|---|---|
| 3,124,136 | A | 3/1964 | Usher |
| 4,347,847 | A | 9/1982 | Usher |
| 4,354,628 | A | 10/1982 | Green |
| 4,452,245 | A | 6/1984 | Usher |
| 4,576,164 | A | 3/1986 | Richeson |
| 4,601,710 | A | 7/1986 | Moll |
| 4,605,730 | A | 8/1986 | Shalaby et al. |
| 4,655,221 | A | 4/1987 | Devereux |
| 4,723,545 | A | 2/1988 | Nixon et al. |
| 4,834,090 | A | 5/1989 | Moore |
| 4,838,884 | A | 6/1989 | Dumican et al. |
| 4,927,640 | A | 5/1990 | Dahlinder et al. |
| 4,930,674 | A | 6/1990 | Barak |
| 5,002,551 | A | 3/1991 | Linsky et al. |

(Continued)

FOREIGN PATENT DOCUMENTS

| CA | 2 667 434 | 5/2008 |
|---|---|---|
| DE | 1 99 24 311 A1 | 11/2000 |

(Continued)

OTHER PUBLICATIONS

Extended European Search Report corresponding to EP No. 12 19 6904.2, completed Mar. 28, 2013, and mailed Jul. 26, 2013; 8 pages.

(Continued)

*Primary Examiner* — Thanh Truong
*Assistant Examiner* — Xavier A Madison

(57) ABSTRACT

A surgical stapling apparatus including a releasable buttress material includes a cartridge assembly, an anvil assembly, and a buttress material. The cartridge assembly includes a plurality of staples, a tissue contacting surface defining staple retaining slots, and a swaged outer edge. The anvil assembly includes a tissue contacting surface defining staple pockets for forming staples expelled from the staple retaining slots of the cartridge assembly. The buttress material has an outer portion that is retaining within the swaged outer edge of the cartridge assembly.

14 Claims, 7 Drawing Sheets

(56) References Cited

U.S. PATENT DOCUMENTS

| | | |
|---|---|---|
| 5,014,899 A | 5/1991 | Presty et al. |
| 5,040,715 A | 8/1991 | Green et al. |
| 5,065,929 A | 11/1991 | Schulze et al. |
| 5,205,459 A | 4/1993 | Brinkerhoff et al. |
| 5,263,629 A | 11/1993 | Trumbull et al. |
| 5,314,471 A | 5/1994 | Brauker et al. |
| 5,344,454 A | 9/1994 | Clarke et al. |
| 5,350,104 A | 9/1994 | Main et al. |
| 5,355,897 A | 10/1994 | Pietrafitta et al. |
| 5,360,154 A | 11/1994 | Green |
| 5,376,376 A | 12/1994 | Li |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk et al. |
| 5,443,198 A | 8/1995 | Viola et al. |
| 5,445,644 A | 8/1995 | Pietrafitta et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,603,698 A | 2/1997 | Roberts et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,187 A | 6/1998 | Sugarbaker |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,895,415 A | 4/1999 | Chow et al. |
| 5,902,312 A | 5/1999 | Frater et al. |
| 5,902,333 A | 5/1999 | Roberts et al. |
| 5,908,427 A | 6/1999 | McKean et al. |
| 5,915,616 A | 6/1999 | Viola et al. |
| 5,931,847 A | 8/1999 | Bittner et al. |
| 5,964,394 A | 10/1999 | Robertson |
| 5,964,774 A | 10/1999 | McKean et al. |
| 5,984,964 A | 11/1999 | Roberts et al. |
| 5,997,895 A | 12/1999 | Narotam et al. |
| 6,019,791 A | 2/2000 | Wood |
| 6,030,392 A | 2/2000 | Dakov et al. |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,117,148 A | 9/2000 | Ravo et al. |
| 6,149,660 A | 11/2000 | Laufer et al. |
| 6,149,667 A | 11/2000 | Hovland et al. |
| 6,155,265 A | 12/2000 | Hammerslag |
| 6,193,129 B1 | 2/2001 | Bittner et al. |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,648,900 B2 | 11/2003 | Fleischman et al. |
| 6,648,901 B2 | 11/2003 | Fleischman et al. |
| 6,652,594 B2 | 11/2003 | Francis et al. |
| 6,656,193 B2 | 12/2003 | Grant et al. |
| 6,669,735 B1 | 12/2003 | Pelissier |
| 6,673,084 B1 | 1/2004 | Peterson et al. |
| 6,677,258 B2 | 1/2004 | Carroll et al. |
| 6,685,714 B2 | 2/2004 | Rousseau |
| 6,702,828 B2 | 3/2004 | Whayne |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,896,684 B2 | 5/2005 | Monassevitch et al. |
| 6,927,315 B1 | 8/2005 | Heinecke et al. |
| 6,939,328 B2 | 9/2005 | Raulerson |
| 6,939,358 B2 | 9/2005 | Palacios et al. |
| 6,946,196 B2 | 9/2005 | Foss |
| 6,959,851 B2 | 11/2005 | Heinrich |
| 7,060,087 B2 | 6/2006 | DiMatteo et al. |
| 7,087,065 B2 | 8/2006 | Ulmsten et al. |
| 7,090,686 B2 | 8/2006 | Nobles et al. |
| 7,108,701 B2 | 9/2006 | Evens et al. |
| 7,128,748 B2 | 10/2006 | Mooradian et al. |
| 7,141,055 B2 | 11/2006 | Abrams et al. |
| 7,147,138 B2 | 12/2006 | Shelton, IV |
| 7,160,299 B2 | 1/2007 | Baily |
| 7,232,449 B2 | 6/2007 | Sharkawy et al. |
| 7,241,300 B2 | 7/2007 | Sharkawy et al. |
| 7,307,031 B2 | 12/2007 | Carroll et al. |
| 7,311,720 B2 | 12/2007 | Mueller et al. |
| 7,334,717 B2 | 2/2008 | Rethy et al. |
| 7,377,928 B2 | 5/2008 | Zubik et al. |
| 7,402,172 B2 | 7/2008 | Chin et al. |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,594,921 B2 | 9/2009 | Browning |
| 7,604,151 B2 | 10/2009 | Hess et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Bettuchi et al. |
| 7,722,642 B2 | 5/2010 | Williamson |
| 7,744,627 B2 | 6/2010 | Orban, III et al. |
| 7,776,060 B2 * | 8/2010 | Mooradian et al. ........... 606/151 |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crows et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban |
| 7,967,179 B2 | 6/2011 | Olson |
| 7,988,027 B2 | 8/2011 | Olson |
| 8,011,550 B2 | 9/2011 | Aranyi |
| 8,016,177 B2 | 9/2011 | Bettuchi |
| 8,016,178 B2 | 9/2011 | Olson |
| 8,028,883 B2 | 10/2011 | Stopek |
| 8,062,330 B2 | 11/2011 | Prommersberger |

(56) References Cited

U.S. PATENT DOCUMENTS

| | | |
|---|---|---|
| 8,083,119 B2 | 12/2011 | Prommersberger |
| 8,123,766 B2 | 2/2012 | Bauman |
| 8,123,767 B2 | 2/2012 | Bauman |
| 8,146,791 B2 | 4/2012 | Bettuchi |
| 8,157,149 B2 | 4/2012 | Olson |
| 8,157,151 B2 | 4/2012 | Ingmanson |
| 8,167,895 B2 | 5/2012 | D'Agostino |
| 8,192,460 B2 | 6/2012 | Orban |
| 8,210,414 B2 | 7/2012 | Bettuchi |
| 8,225,799 B2 | 7/2012 | Bettuchi |
| 8,225,981 B2 | 7/2012 | Criscuolo et al. |
| 8,231,043 B2 | 7/2012 | Tarinelli |
| 8,235,273 B2 | 8/2012 | Olson |
| 8,245,901 B2 | 8/2012 | Stopek |
| 8,256,654 B2 | 9/2012 | Bettuchi et al. |
| 8,257,391 B2 | 9/2012 | Orban |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,348,126 B2 | 1/2013 | Olson |
| 8,348,130 B2 | 1/2013 | Shah |
| 8,365,972 B2 | 2/2013 | Aranyi et al. |
| 8,371,491 B2 | 2/2013 | Huitema |
| 8,371,492 B2 | 2/2013 | Aranyi |
| 8,371,493 B2 | 2/2013 | Aranyi |
| 8,393,514 B2 | 3/2013 | Shelton, IV |
| 8,408,440 B2 | 4/2013 | Olson |
| 8,413,871 B2 | 4/2013 | Racenet |
| 8,424,742 B2 | 4/2013 | Bettuchi |
| 8,453,652 B2 | 6/2013 | Stopek |
| 8,453,904 B2 | 6/2013 | Eskaros |
| 8,453,909 B2 | 6/2013 | Olson |
| 8,453,910 B2 | 6/2013 | Bettuchi |
| 8,464,925 B2 | 6/2013 | Hull et al. |
| 8,474,677 B2 | 7/2013 | Woodard, Jr. |
| 8,479,968 B2 | 7/2013 | Hodgkinson |
| 8,485,414 B2 | 7/2013 | Criscuolo et al. |
| 8,496,683 B2 | 7/2013 | Prommersberger |
| 8,511,533 B2 | 8/2013 | Viola |
| 8,512,402 B2 | 8/2013 | Marczyk |
| 8,529,600 B2 | 9/2013 | Woodard, Jr. et al. |
| 8,540,131 B2 | 9/2013 | Swayze |
| 8,551,138 B2 | 10/2013 | Orban |
| 8,556,918 B2 | 10/2013 | Bauman |
| 8,561,873 B2 | 10/2013 | Ingmanson |
| 8,584,920 B2 | 11/2013 | Hodgkinson |
| 8,590,762 B2 | 11/2013 | Hess |
| 8,616,430 B2 | 12/2013 | Prommersberger |
| 8,631,989 B2 | 1/2014 | Aranyi |
| 8,668,129 B2 | 3/2014 | Olson |
| 8,684,250 B2 | 4/2014 | Bettuchi |
| 8,757,466 B2 | 6/2014 | Olson |
| 8,789,737 B2 | 7/2014 | Hodgkinson |
| 8,820,606 B2 | 9/2014 | Hodgkinson |
| 2002/0028243 A1 | 3/2002 | Masters |
| 2002/0091397 A1 | 7/2002 | Chen |
| 2002/0173809 A1 | 11/2002 | Fleischman et al. |
| 2003/0028178 A1 | 2/2003 | Chin |
| 2003/0065345 A1 | 4/2003 | Weadock |
| 2003/0083676 A1 | 5/2003 | Wallace |
| 2003/0120284 A1 | 6/2003 | Palacios |
| 2003/0144686 A1 | 7/2003 | Martinez et al. |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0068278 A1 | 4/2004 | Fleischman et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2005/0228413 A1 | 10/2005 | Binmoeller et al. |
| 2005/0228446 A1 | 10/2005 | Mooradian et al. |
| 2006/0004407 A1 | 1/2006 | Hiles et al. |
| 2006/0030877 A1 | 2/2006 | Martinez et al. |
| 2006/0129165 A1 | 6/2006 | Edoga et al. |
| 2006/0135992 A1 | 6/2006 | Bettuchi |
| 2006/0173470 A1 | 8/2006 | Oray et al. |
| 2006/0178683 A1 | 8/2006 | Shimoji et al. |
| 2006/0229643 A1 | 10/2006 | Nolan et al. |
| 2006/0264986 A1 | 11/2006 | Park et al. |
| 2006/0271104 A1 | 11/2006 | Viola et al. |
| 2007/0005084 A1 | 1/2007 | Clague et al. |
| 2007/0021840 A1 | 1/2007 | Lopera |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 * | 7/2008 | Bauman et al. ............... 606/148 |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |

(56) References Cited

U.S. PATENT DOCUMENTS

| | | |
|---|---|---|
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0215132 A1 | 9/2011 | Aranyi |
| 2012/0012637 A1* | 1/2012 | Bettuchi et al. ............ 227/175.1 |
| 2012/0074199 A1 | 3/2012 | Olson |
| 2012/0080336 A1 | 4/2012 | Shelton |
| 2012/0187179 A1 | 7/2012 | Gleiman |
| 2012/0241499 A1 | 9/2012 | Baxter |
| 2012/0273547 A1 | 11/2012 | Hodgkinson et al. |
| 2013/0037596 A1 | 2/2013 | Bear et al. |
| 2013/0105548 A1 | 5/2013 | Hodgkinson |
| 2013/0105553 A1 | 5/2013 | Racenet |
| 2013/0112732 A1 | 5/2013 | Aranyi |
| 2013/0112733 A1 | 5/2013 | Aranyi |
| 2013/0146641 A1 | 6/2013 | Shelton |
| 2013/0153633 A1 | 6/2013 | Casasanta |
| 2013/0153634 A1 | 6/2013 | Carter |
| 2013/0153635 A1 | 6/2013 | Hodgkinson |
| 2013/0153636 A1 | 6/2013 | Shelton |
| 2013/0153638 A1 | 6/2013 | Carter |
| 2013/0153639 A1 | 6/2013 | Hodgkinson |
| 2013/0153640 A1 | 6/2013 | Hodgkinson |
| 2013/0153641 A1 | 6/2013 | Shelton |
| 2013/0161374 A1 | 6/2013 | Swayze |
| 2013/0181031 A1 | 7/2013 | Olson |
| 2013/0193186 A1 | 8/2013 | Racenet |
| 2013/0193190 A1 | 8/2013 | Carter |
| 2013/0193191 A1 | 8/2013 | Stevenson |
| 2013/0193192 A1 | 8/2013 | Casasanta |
| 2013/0209659 A1 | 8/2013 | Racenet |
| 2013/0221062 A1 | 8/2013 | Hodgkinson |
| 2013/0240600 A1 | 9/2013 | Bettuchi |
| 2013/0240601 A1 | 9/2013 | Bettuchi |
| 2013/0240602 A1 | 9/2013 | Stopek |
| 2013/0277411 A1 | 10/2013 | Hodgkinson |
| 2013/0306707 A1 | 11/2013 | Viola |
| 2013/0310873 A1 | 11/2013 | Stopek et al. |
| 2013/0327807 A1 | 12/2013 | Olson |
| 2014/0012317 A1 | 1/2014 | Orban |
| 2014/0021242 A1 | 1/2014 | Hodgkinson |
| 2014/0027490 A1 | 1/2014 | Marczyk |
| 2014/0034704 A1 | 2/2014 | Ingmanson |
| 2014/0048580 A1 | 2/2014 | Merchant |
| 2014/0061280 A1 | 3/2014 | Ingmanson |
| 2014/0061281 A1 | 3/2014 | Hodgkinson |
| 2014/0084042 A1 | 3/2014 | Stopek |
| 2014/0097224 A1 | 4/2014 | Prior |
| 2014/0117066 A1 | 5/2014 | Aranyi |
| 2014/0130330 A1 | 5/2014 | Olson |
| 2014/0131418 A1 | 5/2014 | Kostrzewski |
| 2014/0131419 A1 | 5/2014 | Bettuchi |
| 2014/0138423 A1 | 5/2014 | Whitfield |
| 2014/0151431 A1 | 6/2014 | Hodgkinson |
| 2014/0155916 A1 | 6/2014 | Hodgkinson |
| 2014/0158742 A1 | 6/2014 | Stopek |
| 2014/0166721 A1 | 6/2014 | Stevenson |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson |

FOREIGN PATENT DOCUMENTS

| | | |
|---|---|---|
| DE | 199 24 311 A1 | 11/2000 |
| EP | 0 594 148 A1 | 4/1994 |
| EP | 0 327 022 B1 | 4/1995 |
| EP | 0 667 119 A1 | 8/1995 |
| EP | 1 064 883 A1 | 1/2001 |
| EP | 1 256 317 A2 | 11/2002 |
| EP | 1 256 318 | 11/2002 |
| EP | 1 520 525 A1 | 4/2005 |
| EP | 1 621 141 A2 | 2/2006 |
| EP | 1 702 570 A1 | 9/2006 |
| EP | 1 759 640 A2 | 3/2007 |
| EP | 1 815 804 A2 | 8/2007 |
| EP | 1 825 820 | 9/2007 |
| EP | 1 929 958 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 090 231 | 8/2009 |
| EP | 2 090 244 | 8/2009 |
| EP | 2 090 252 | 8/2009 |
| EP | 2 198 787 A1 | 6/2010 |
| EP | 2 236 098 A2 | 10/2010 |
| EP | 2 236 099 | 10/2010 |
| EP | 2 311 386 | 4/2011 |
| EP | 2 436 348 | 4/2012 |
| EP | 2 462 880 | 6/2012 |
| EP | 2 517 637 | 10/2012 |
| EP | 2 586 380 | 5/2013 |
| EP | 2 604 195 | 6/2013 |
| EP | 2 604 197 | 6/2013 |
| EP | 2 620 106 | 7/2013 |
| EP | 2 630 922 | 8/2013 |
| EP | 2 644 125 | 10/2013 |
| JP | 2000-166933 | 6/2000 |
| JP | 2002-202213 | 7/2002 |
| JP | 07-124166 | 5/2007 |
| WO | WO 90/05489 A1 | 5/1990 |
| WO | WO 95/16221 | 6/1995 |
| WO | WO 96/22055 A1 | 7/1996 |
| WO | WO 97/01989 A1 | 1/1997 |
| WO | WO 97/13463 A1 | 4/1997 |
| WO | WO 98/17180 A1 | 4/1998 |
| WO | WO 99/45849 A1 | 9/1999 |
| WO | WO 01/21060 A1 | 3/2001 |
| WO | WO 02/00121 A1 | 1/2002 |
| WO | WO 03/082126 A1 | 10/2003 |
| WO | WO 03/088845 | 10/2003 |
| WO | WO 03/094743 | 11/2003 |
| WO | WO 03/105698 A2 | 12/2003 |
| WO | WO 2005/079675 | 9/2005 |
| WO | WO 2006/023578 A2 | 3/2006 |
| WO | WO 2006/044490 A2 | 4/2006 |
| WO | WO 2006/083748 A1 | 8/2006 |
| WO | WO 2007/121579 A1 | 11/2007 |
| WO | WO 2007/147439 A1 | 12/2007 |
| WO | WO 2008/057281 A2 | 5/2008 |
| WO | WO 2008/109125 A1 | 9/2008 |
| WO | WO 2010/075298 A2 | 7/2010 |
| WO | WO 2011/143183 A2 | 11/2011 |
| WO | WO 2012/044848 A1 | 4/2012 |

OTHER PUBLICATIONS

International Search Report corresponding to European Application No. EP 12 15 2229.6, completed on Feb. 23, 2012 and mailed on Mar. 1, 2012; 4 pages.

International Search Report corresponding to European Application No. EP 12 15 0511.9, completed on Apr. 16, 2012 and mailed on Apr. 24, 2012; 7 pages.

International Search Report corresponding to European Application No. EP 12 15 2541.4, completed on Apr. 23, 2012 and mailed on May 3, 2012; 10 pages.

International Search Report corresponding to European Application No. EP 12 16 5609.4, completed on Jul. 5, 2012 and mailed on Jul. 13, 2012; 8 pages.

(56) References Cited

OTHER PUBLICATIONS

International Search Report corresponding to European Application No. EP 12 15 8861.0, completed on Jul. 17, 2012 and mailed on Jul. 24, 2012; 9 pages.
International Search Report corresponding to European Application No. EP 12 16 5878.5, completed on Jul. 24, 2012 and mailed on Aug. 6, 2012; 8 pages.
Extended European Search Report corresponding to EP 12 19 1035. 0, completed Jan. 11, 2013 and mailed Jan. 18, 2013, 7 pages.
Extended European Search Report corresponding to EP 12 19 8749. 9, completed May 21, 2013 and mailed May 31, 2013; 8 pages.
Copy of Extended European Search Report corresponding to EP 07 00 5842.5, completed May 13, 2013 and mailed May 29, 2013; 7 pages.
Extended European Search Report corresponding to EP 12 19 8776. 2, completed May 16, 2013 and mailed May 27, 2013; 8 pages.
Extended European Search Report corresponding to EP 13 15 6297,7, completed Jun. 4, 2013 and mailed Jun. 13, 2013; 7 pages.
Extended European Search Report corresponding to EP 13 17 3985. 6, completed Aug. 19, 2013 and mailed Aug. 28, 2013; 6 pages.
Extended European Search Report corresponding to EP 13 17 3986. 4, completed Aug. 20, 2013 and mailed Aug. 29, 2013; 7 pages.
Extended European Search Report corresponding to EP 13 18 3876. 5, completed Oct. 14, 2013 and mailed Oct. 24, 2013; 5pp.
Extended European Search Report corresponding to EP No. 12 19 1035.0, completed Jan. 11, 2013 and mailed Jan. 18, 2013; 7 pages.
Extended European Search Report corresponding to EP No. 12 18 6175.1, completed Jan. 15, 2013 and mailed Jan. 23, 2013; 7 pages.
Extended European Search Report corresponding to EP No. 12 19 1114.3, completed Jan. 23, 2013 and mailed Jan. 31, 2013; 10 pages.
Extended European Search Report corresponding to EP No. 12 19 2224.9, completed Mar. 14, 2013 and mailed Mar. 26, 2013; 8 pages.
Extended European Search Report corresponding to EP No. 12 19 6911.7, completed Apr. 18, 2013 and mailed Apr. 24, 2013; 8 pages.
International Search Report corresponding to European Application No. EP 05 02 2585.3, completed on Jan. 25, 2006 and mailed on Feb. 3, 2006; 4 pages.
International Search Report corresponding to European Application No. EP 06 00 4598, completed on Jun. 22, 2006; 2 pages.
International Search Report corresponding to European Application No. EP 06 01 6962.0, completed on Jan. 3, 2007 and mailed on Jan. 11, 2007; 10 pages.
International Search Report corresponding to International Application No. PCT/US05/36740, completed on Feb. 20, 2007 and mailed on Mar. 23, 2007; 8 pages.
International Search Report corresponding to International Application No. PCT/US2007/022713, completed on Apr. 21, 2008 and mailed on May 15, 2008; 1 page.
International Search Report corresponding to International Application No. PCT/US2008/002981, completed on Jun. 9, 2008 and mailed on Jun. 26, 2008; 2 pages.
International Search Report corresponding to European Application No. EP 08 25 1779, completed on Jul. 14, 2008 and mailed on Jul. 23, 2008; 5 pages.
International Search Report corresponding to European Application No. EP 08 25 1989.3, completed on Mar. 11, 2010 and mailed on Mar. 24, 2010; 6 pages.
International Search Report corresponding to European Application No. EP 10 25 0639.1, completed on Jun. 17, 2010 and mailed on Jun. 28, 2010; 7 pages.
International Search Report corresponding to European Application No. EP 10 25 0715.9, completed on Jun. 30, 2010 and mailed on Jul. 20, 2010; 3 pages.
International Search Report corresponding to European Application No. EP 05 80 4382.9, completed on Oct. 5, 2010 and mailed on Oct. 12, 2010; 3 pages.
International Search Report corresponding to European Application No. EP 10 25 1437.9, completed on Nov. 22, 2010 and mailed on Dec. 16, 2010; 3 pages.
International Search Report corresponding to European Application No. EP 09 25 2897.5, completed on Feb. 7, 2011 and mailed on Feb. 15, 2011; 3 pages.
International Search Report corresponding to European Application No. EP 10 25 0642.5, completed on Mar. 25, 2011 and mailed on Apr. 4, 2011; 4 pages.
International Search Report corresponding to European Application No. EP 11 18 8309.6, completed on Dec. 15, 2011 and mailed on Jan. 12, 2012; 3 pages.
Extended European Search Report corresponding to EP 13 17 7437. 4, completed Sep. 11, 2013 and mailed Sep. 19, 2013; (6 pp).
Extended European Search Report corresponding to EP 13 17 7441. 6, completed Sep. 11, 2013 and mailed Sep. 19, 2013; (6 pp).
Extended European Search Report corresponding to EP 07 86 1534. 1, completed Sep. 20, 2013 and mailed Sep. 30, 2013; (5 pp).
Extended European Search Report corresponding to EP 13 17 1856. 1, completed Oct. 29, 2013 and mailed Nov. 7, 2013; (8 pp).
Extended European Search Report corresponding to EP 13 18 0373. 6, completed Oct. 31, 2013 and mailed Nov. 13, 2013; (7 pp).
Extended European Search Report corresponding to EP 13 18 0881. 8, completed Nov. 5, 2013 and mailed Nov. 14, 2013; (6 pp).
Extended European Search Report corresponding to EP 13 17 6895. 4, completed Nov. 29, 2013 and mailed Dec. 12, 2013; (5 pp).
Extended European Search Report corresponding to EP 13 18 2911. 1, completed Dec. 2, 2013 and mailed Dec. 16, 2013; (8 pp).
Extended European Search Report corresponding to EP 10 25 1795. 0, completed Dec. 11, 2013 and mailed Dec. 20, 2013; (6 pp).
Extended European Search Report corresponding to EP 13 18 7911. 6, completed Jan. 22, 2014 and mailed Jan. 31, 2014; (8 pp).
Extended European Search Report corresponding to EP 08 72 6500. 5, completed Feb. 20, 2014 and mailed Mar. 3, 2014; (7 pp).
Extended European Search Report corresponding to EP 13 19 5919. 9, completed Feb. 10, 2014 and mailed Mar. 3, 2014; (7 pp).
Extended European Search Report corresponding to EP 13 19 2123. 1, completed Jan. 30, 2014 and mailed Feb. 10, 2014; (8 pp).
Extended European Search Report corresponding to EP 13 19 6816. 6, completed Mar. 28, 2014 and mailed Apr. 9, 2014; (9 pp).
Extended European Search Report corresponding to EP 13 19 4995. 0, completed Jun. 5, 2014 and mailed Jun. 16, 2014; (5 pp).
Extended European Search Report corresponding to EP 13 19 5019. 8, completed Mar. 14, 2014 and mailed Mar. 24, 2014; (7 pp).
Extended European Search Report corresponding to EP 13 19 2111. 6, completed Feb. 13, 2014 and mailed Feb. 27, 2014; (10 pp).
Extended European Search Report corresponding to EP 13 19 7958. 5, completed Apr. 4, 2014 and mailed Apr. 15, 2014; (8 pp).
Extended European Search Report corresponding to EP 14 15 6342. 9, completed Jul. 22, 2014 and mailed Jul. 29, 2014; (8 pp).
Extended European Search Report corresponding to EP 14 15 7195. 0, completed Jun. 5, 2014 and mailed Jun. 18, 2014; (9 pp).

\* cited by examiner

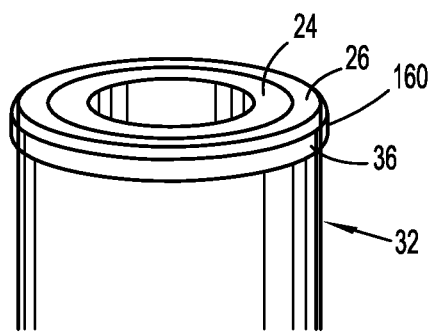
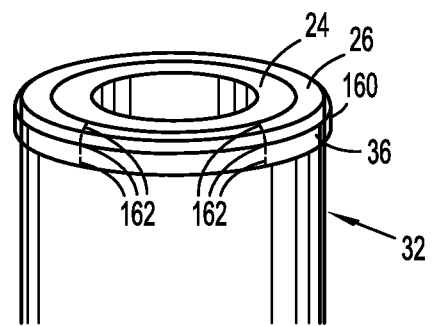
FIG. 8A  FIG. 8B
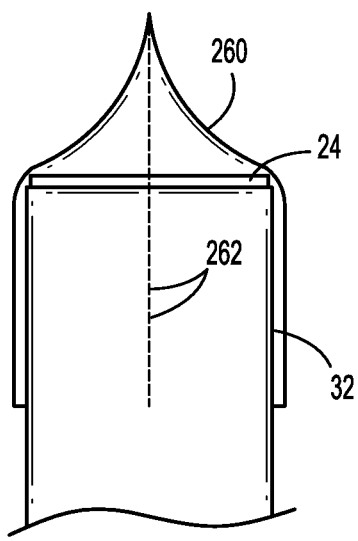
FIG. 9

RELEASABLE BUTTRESS RETENTION ON A SURGICAL STAPLER

BACKGROUND

1. Technical Field

The present disclosure relates to surgical stapling apparatus including surgical buttresses which can be releasably attached to the surgical stapling apparatus, and in particular, to surgical stapling apparatus having a surgical buttress temporarily secured to an anvil and/or staple cartridge assembly of the surgical stapling apparatus.

2. Background of Related Art

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the stapling apparatus is actuated, or "fired", longitudinally moving firing bars contact staple drive members in one of the jaws. The staple drive members push the surgical staples through the body tissue and into an anvil in the opposite jaw which forms the staples. If tissue is to be removed or separated, a knife blade can be provided in the jaws of the apparatus to cut the tissue between the lines of staples.

A number of surgical stapling apparatus rely on knife blade cutting of some portion of the buttress material to effect buttress release. These methods may employ a secondary material or mounting structure in addition to the buttress material to provide attachment to the surgical stapling apparatus. Typically, firing forces are increased with each material that must be transected by the knife blade in order to release the buttress. For example, WO 08/109125 discloses a surgical stapling apparatus that includes a surgical buttress releasably secured by an anchor.

It would be desirable to provide a buttress that may be releasably secured to a surgical stapling apparatus without the need for a secondary material or mounting structure, and without the need for a knife blade to cut the buttress and/or secondary material or mounting structure to release the buttress from the surgical stapling apparatus, thereby resulting in the use of few materials and lower firing forces.

SUMMARY

According to an aspect of the present disclosure, a surgical stapling apparatus including a releasable buttress material includes a cartridge assembly, an anvil assembly, and a buttress material. The cartridge assembly includes a plurality of staples, a tissue contacting surface defining staple retaining slots, and a swaged outer edge. The anvil assembly includes a tissue contacting surface defining staple pockets for forming staples expelled from the staple retaining slots of the cartridge assembly. The buttress material has an outer portion retained within the swaged outer edge of the cartridge assembly. In some embodiments, the buttress material may include slits. In some embodiments, the outer portion of the buttress material may be frayed.

The swaged outer edge of the cartridge assembly may include a rim overlapping the tissue contacting surface of the cartridge assembly in spaced relation therewith and defining an inner pocket between the tissue contacting surface and the rim. In embodiments, the rim continuously extends around the entire perimeter of the buttress material. In other embodiments, the rim includes a plurality of discontinuous tabs extending around the buttress material. In some embodiments, the rim may include sharp edges extending radially inward of the outer edge.

The anvil assembly may include a swaged outer edge and a buttress material retained within the swaged outer edge of the anvil assembly. The swaged outer edge of the anvil assembly may include a rim overlapping the tissue contacting surface of the anvil assembly in spaced relation therewith and defining an inner pocket between the tissue contacting surface and the rim. In some embodiments, the buttress material retained within the swaged outer edge of the anvil assembly may include slits. In some embodiments, the outer portion of the buttress material retained within the swaged outer edge of the anvil assembly may be frayed. The buttress material of the anvil assembly may be different from the buttress material of the cartridge assembly.

In embodiments, the cartridge assembly is associated with a body portion of the surgical stapling apparatus and the anvil assembly includes a shaft removably mountable to the body portion, the anvil assembly being movable toward and away from the body portion. In such embodiments, the cartridge assembly and the anvil assembly may be circular, and the buttress material may include a central opening dimensioned to receive the shaft of the anvil assembly.

In embodiments, the cartridge assembly is associated with a first jaw and the anvil assembly is associated with a second jaw, the first and second jaws being selectively movable relative to one another from a first spaced apart position to a second position wherein the first and second jaws cooperate to grasp tissue therebetween.

Accordingly to another aspect of the present disclosure, a surgical stapling apparatus including a releasable buttress material includes a cartridge assembly, an anvil assembly, and a buttress material. The cartridge assembly includes a plurality of staples and a tissue contacting surface defining staple retaining slots. The anvil assembly includes a tissue contacting surface defining staple pockets for forming staples expelled from the staple retaining slots of the cartridge assembly, and a swaged outer edge. The swaged outer edge of the anvil assembly may include a rim overlapping the tissue contacting surface of the anvil assembly in spaced relation therewith and defining an inner pocket between the tissue contacting surface and the rim. The buttress material has an outer portion retained within the swaged outer edge of the anvil assembly. In some embodiments, the buttress material may include slits. In some embodiments, the outer portion of the buttress material may be frayed.

According to yet another aspect of the present disclosure, a surgical stapling apparatus including a releasable buttress material includes a cartridge assembly including a plurality of staples and a tissue contacting surface defining staple retaining slots, an anvil assembly including a tissue contacting surface defining staple pockets for forming staples expelled from the staple retaining slots of the cartridge assembly, a knife disposed within a knife slot formed in the tissue contacting surface of the cartridge assembly, and a buttress material having an outer portion swaged to an outer edge of one of the cartridge assembly and the anvil assembly.

BRIEF DESCRIPTION OF THE DRAWINGS

Embodiments of the presently disclosed surgical stapling apparatus and surgical buttress are described herein with reference to the accompanying drawings, wherein:

FIGS. 8A and 8B are perspective views of a surgical buttress secured to a staple cartridge assembly in accordance with embodiments of the present disclosure;

FIG. 9 is a schematic side view of a surgical buttress secured to a staple cartridge assembly in accordance with another embodiment of the present disclosure;

DETAILED DESCRIPTION OF THE EMBODIMENTS

Figure 1:
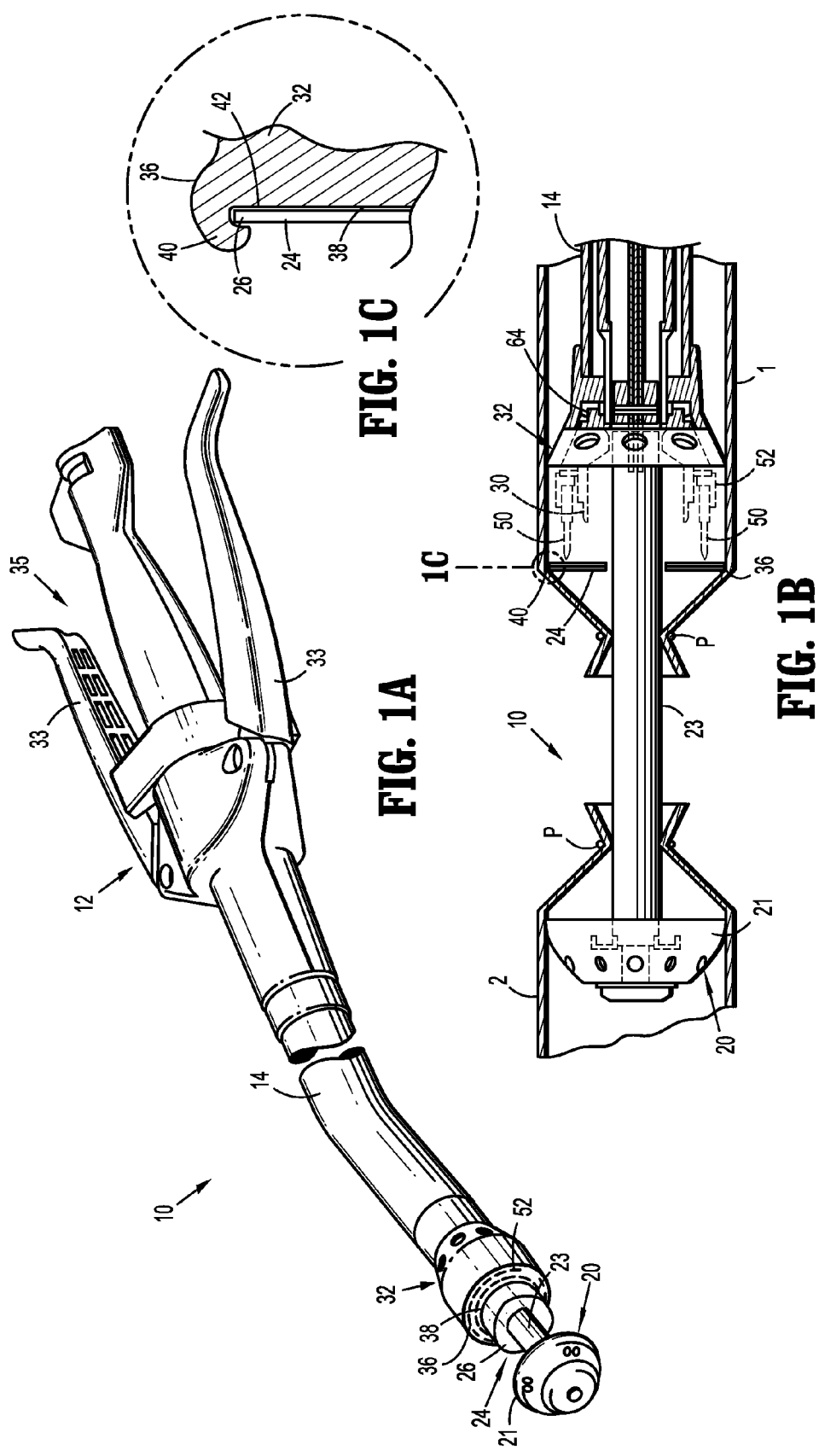
FIG. 1A is a perspective view of an illustrative embodiment of a surgical stapling apparatus and surgical buttress (shown separated from a staple cartridge assembly of the surgical stapling apparatus) in accordance with an embodiment of the present disclosure.
FIG. 1B is a partial, longitudinal cross-sectional view of the surgical stapling apparatus of FIG. 1A including a surgical buttress positioned thereon and shown disposed within an intestinal area.
FIG. 1C is an enlarged cross-sectional view of the area of detail indicated in FIG. 1B.

Various exemplary embodiments of the present disclosure are discussed herein below in terms of surgical buttresses for use with surgical stapling apparatus. The surgical buttresses described herein may be used in closing a wound by approximating the edges of wound tissue between a staple cartridge and an anvil of a surgical stapling apparatus which contains at least one buttress. The at least one buttress is joined to the surgical stapling apparatus by a swaged outer edge of an anvil and/or staple cartridge assembly which captures an outer portion of the surgical buttress to retain the surgical buttress therein. Staples fired from the surgical stapling apparatus attach the surgical buttress to tissue and maintain a force on the surgical buttress to allow the surgical buttress to slip out from under the outer edge of the anvil and/or staple cartridge assembly as the surgical stapling apparatus is pulled away from the anastomosed site, releasing the surgical buttress from the surgical stapling apparatus. Thus, the present disclosure describes surgical buttresses, surgical stapling apparatus supporting said surgical buttresses, and methods and mechanisms for using the same.

It should be understood that a variety of surgical stapling apparatus may be utilized with a surgical buttress of the present disclosure. For example, linear stapler configurations may be utilized, such as, for example those including Duet TRS™ reloads and staplers with Tri-Staple™ technology, available through Covidien, which maintain a principal place of business at 555 Long Wharf Drive, North Haven, Conn. 06511, and transverse anastomosis staplers, such as, for example, EEA™, CEEA™, GIA™, EndoGIA™, and TA™ staplers, available through Covidien. It should also be appreciated that the principles of the present disclosure are equally applicable to surgical staplers having alternate configurations, such as, for example, end-to-end anastomosis staplers having a circular cartridge and anvil (see, e.g., commonly owned U.S. Pat. No. 5,915,616, entitled "Surgical Fastener Applying Apparatus," the entire content of which is incorporated herein by this reference); laparoscopic staplers (see, e.g., commonly owned U.S. Pat. Nos. 6,330,965 and 6,241,139, each entitled "Surgical Stapling Apparatus," the entire contents of each of which being incorporated herein by this reference); and transverse anastomosis staplers (see, e.g., commonly owned U.S. Pat. Nos. 5,964,394 and 7,334,717, each entitled "Surgical Fastener Applying Apparatus", the entire contents of each of which being incorporated herein by this reference).

Embodiments of the presently disclosed surgical buttress and surgical stapling apparatus will now be described in detail with reference to the drawing figures wherein like reference numerals identify similar or identical elements. In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse, or other care provider and may include support personnel.

Referring now to FIGS. 1A and 1B, there is disclosed an exemplary surgical stapling apparatus or surgical stapler 10 for use in stapling tissue and applying a buttress material or surgical buttress to the tissue. Surgical stapling apparatus 10 generally includes a handle assembly 12 having at least one pivotable actuating handle member 33, and an advancing member 35. Extending from handle member 12, there is provided a tubular body portion 14 which may be constructed so as to have a curved shape along its length. Body portion 14 terminates in a staple cartridge assembly 32 which includes an annular array of staple retaining slots 52 having a staple 50 disposed in each one of staple retaining slots 52. Positioned distally of staple cartridge assembly 32 there is provided an anvil assembly 20 including an anvil member 21 and a shaft 23 operatively associated therewith for removably connecting anvil assembly 20 to a distal end portion of stapling apparatus 10.

Staple cartridge assembly 32 may be fixedly connected to the distal end of tubular body portion 14 or may be configured to concentrically fit within the distal end of tubular body portion 14. Typically, staple cartridge assembly 32 includes a staple pusher 64 including a proximal portion having a generally frusto-conical shape and a distal portion defining concentric rings of peripherally spaced fingers (not shown), each one of which is received within a respective staple retaining slot 52. For example, the staple pusher of the staple cartridge assembly can have two concentric rings of fingers.

A knife 30, substantially in the form of an open cup with the rim thereof defining a knife blade 31, is disposed within staple cartridge assembly 32 and mounted to a distal surface of a staple pusher 64. The knife 30 is disposed radially inward of the annular arrays of staples 50. Accordingly, in use, as the staple pusher 64 is advanced, the knife 30 is also advanced axially outward.

Reference may be made to commonly owned U.S. Pat. No. 5,915,616 to Viola et al., referenced above, for a detailed discussion of the construction and operation of an annular stapling device.

Figure 3:
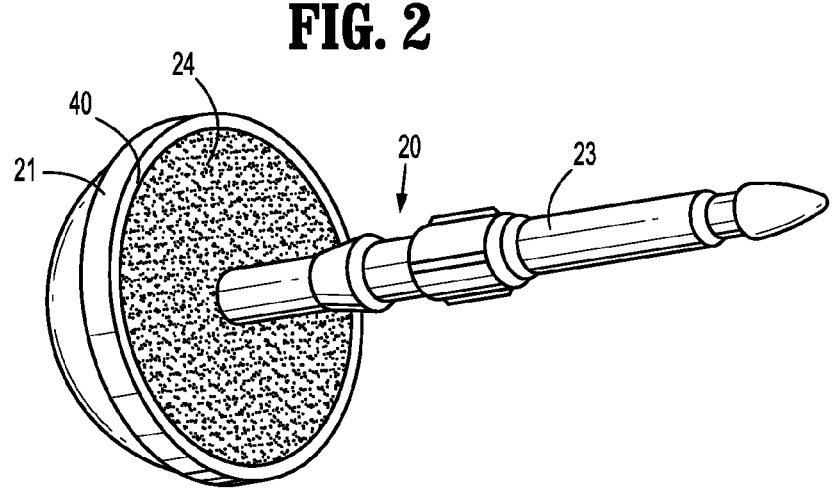
FIG. 3 is a perspective view of a surgical buttress in accordance with an embodiment of the present disclosure attached to an anvil assembly.

A surgical buttress 24 is releasably attached to the staple cartridge assembly 32 by an overlapping outer edge 36 of the staple cartridge assembly 32 that is swaged, molded or otherwise formed to entrap an outer portion 26 of the surgical buttress 24 between a rim 40 and a tissue contacting/facing surface 38 of staple cartridge assembly 32. It should be understood that while the surgical buttress 24 is described herein as being associated with the staple cartridge assembly 32, the surgical buttress 24 may, alternatively or additionally, be associated with the anvil assembly 20, as illustrated in FIG. 3. Surgical buttress 24 is provided to reinforce and/or seal staple lines applied to tissue by surgical stapling apparatus 10. Surgical buttress 24 may be configured into any shape, size, or dimension suitable to fit any surgical stapling, fastening, or firing apparatus.

Surgical buttress 24 is fabricated from a biocompatible material which is a bioabsorbable or non-absorbable, natural or synthetic material. It should of course be understood that any combination of natural, synthetic, bioabsorbable, and non-bioabsorbable materials may be used to form the surgical buttress. In embodiments, the entire surgical buttress 24, or portions thereof, may be fabricated from the same material, or combination of materials that is homogeneous throughout the surgical buttress 24. In other embodiments, the surgical buttress 24 may be formed of different materials.

The surgical buttress 24 may be porous, non-porous, or combinations thereof. It is also envisioned that surgical buttress 24 described herein may contain a plurality of layers in which any combination of non-porous and porous layers may be configured as discussed further below. For example, surgical buttress may be formed to include multiple non-porous layers and porous layers that are stacked in an alternating manner. In another example, surgical buttress may be formed in a "sandwich-like" manner wherein the outer layers of the surgical buttress include porous layers and the inner layers are non-porous layers. It is further envisioned that non-porous and porous layers may be positioned in any order relative to the tissue contacting surfaces of the staple cartridge/anvil assembly. Examples of multilayered surgical buttresses are disclosed in U.S. Patent Application Publication No. 2009/0001122 filed Jun. 27, 2007, entitled "Buttress and Surgical Stapling Apparatus," the entire disclosure of which is incorporated by reference herein.

Some non-limiting examples of materials from which non-porous and/or porous layers of surgical buttress 24 may be made include, but are not limited to, poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends, and combinations thereof.

In embodiments, natural biological polymers are used in forming a non-porous layer of the surgical buttress. Suitable natural biological polymers include, but are not limited to, collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethyl cellulose, chitan, chitosan, and combinations thereof. In addition, the natural biological polymers may be combined with any of the other polymeric materials described herein to produce a non-porous layer of the surgical buttress.

In embodiments, collagen of human and/or animal origin, e.g., type I porcine or bovine collagen, type I human collagen or type III human collagen, may be used to form a non-porous layer of the surgical buttress. In embodiments, a non-porous layer of the surgical buttress according to the present disclosure is made of collagen which is oxidized or a mixture in any proportions of non-oxidized and oxidized collagens.

The use of non-porous layer(s) in the surgical buttress may enhance the ability of the surgical buttress to resist tears and perforations during the manufacturing, shipping, handling, and stapling processes. Also, the use of a non-porous layer in the surgical buttress may also retard or prevent tissue ingrowth from surrounding tissues thereby acting as an adhesion barrier and preventing the formation of unwanted scar tissue. Thus, in embodiments, the non-porous layer(s) of the surgical buttress may possess anti-adhesion properties.

A non-porous layer of the surgical buttress may be formed using techniques within the purview of those skilled in the art, such as casting, molding, and the like.

Any of the porous layers of the surgical buttress may have openings or pores over at least a portion of a surface thereof. As described in more detail below, suitable materials for forming a porous layer include, but are not limited to, fibrous structures (e.g., knitted structures, woven structures, non-woven structures, etc.) and/or foams (e.g., open or closed cell foams). In embodiments, the pores may be in sufficient number and size so as to interconnect across the entire thickness of the porous layer. Woven fabrics, knitted fabrics, and open cell foam are illustrative examples of structures in which the pores can be in sufficient number and size so as to interconnect across the entire thickness of the porous layer. In embodiments, the pores may not interconnect across the entire thickness of the porous layer, but rather may be present at a portion thereof. Thus, in some embodiments, pores may be located on a portion of the porous layer, with other portions of the porous layer having a non-porous texture. Those skilled in the art reading the present disclosure will envision a variety of pore distribution patterns and configurations for the porous layer. Closed cell foam or fused non-woven materials are illustrative examples of structures in which the pores may not interconnect across the entire thickness of the porous layer.

Where a porous layer of the surgical buttress is fibrous, the fibers may be filaments or threads suitable for knitting or weaving or may be staple fibers, such as those frequently used for preparing non-woven materials. Woven, non-woven, drawing, knitting, and other known techniques can be used to make the surgical buttress. Suitable techniques for making fibrous structures are within the purview of those skilled in the art.

Where a porous layer of the surgical buttress is a foam, the porous layer may be formed using any method suitable to forming a foam or sponge including, but not limited to, the lyophilization or freeze-drying of a composition. Suitable techniques for making foams are within the purview of those skilled in the art.

The origin and types of collagens that may be used to form the porous layer are the same as those indicated above for the non-porous layer. However, the oxidized or non-oxidized collagen may be lyophilized, freeze-dried, or emulsified in the presence of a volume of air to create a foam and then freeze-dried, to form a porous compress.

In embodiments, a porous layer of the surgical buttress may be made from denatured collagen or collagen which has at least partially lost its helical structure through heating or any other method. The term "denatured collagen" means collagen which has lost its helical structure. The collagen used for the porous layer as described herein may be native collagen or atellocollagen. The collagen may have been previously chemically modified by oxidation, methylation, succinylation, ethylation, or any other known process.

The porous layer(s) may enhance the ability of the surgical buttress to absorb fluid, reduce bleeding, and seal the wound. Also, the porous layer(s) may allow for tissue ingrowth to fix the surgical buttress in place.

Referring again to FIGS. 1B and 1C, staple cartridge 32 includes an outer edge 36 extending in a "c" or "u" shape to form a rim 40 which overlaps the tissue contacting surface 38 of the staple cartridge assembly 32 in spaced relation to define an inner pocket 42 that is dimensioned to releasably retain an outer portion 26 of the surgical buttress 24 against the tissue contacting surface 38 of the staple cartridge 32. While the rim 40 is shown as continuously extending around the entire perimeter of the surgical buttress, it should be understood that the rim 40 may be discontinuous and include a plurality of tabs 41 extending around the surgical buttress 24, such as in the configuration illustrated in FIG. 2, for example. It is envisioned that the outer edge 36 may be swaged by pinching, crimping, or otherwise deforming at least a portion of the outer edge 36 to capture at least a portion of the surgical buttress 24. The outer edge may be swaged, molded or otherwise formed.

Figure 2:
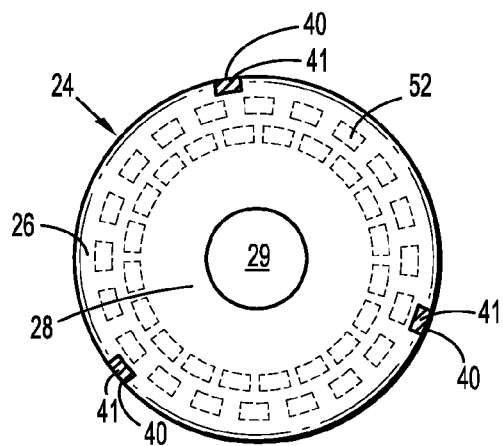
FIG. 2 is a top plan view of a surgical buttress in accordance with another embodiment of the present disclosure illustrating its attachment to a surgical stapling apparatus.

As illustrated in FIG. 2, surgical buttress 24 includes an inner portion 28 defining an aperture 29 to receive shaft 23 of anvil assembly 20 and an outer portion 26 extending under the rim 40 of the outer edge 36 (FIGS. 1A-1C) of the staple cartridge assembly 32.

Figure 4A:
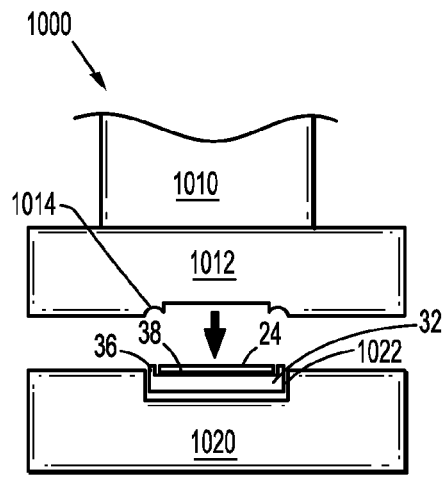
FIGS. 4A and 4B are cross-sectional views of a staple cartridge of the surgical stapling apparatus and a surgical buttress of the present disclosure, illustrating an exemplary process of forming a swaged outer edge in accordance with an embodiment of the present disclosure.
Figure 4B:
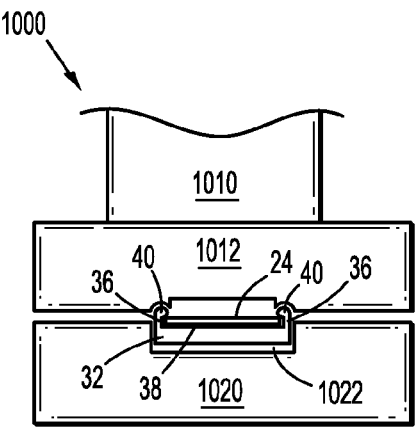

With reference now to FIGS. 4A and 4B, a method of swaging the outer edge 36 of the staple cartridge assembly 32 (or anvil assembly 20) for retaining a surgical buttress 24 is illustrated. The staple cartridge assembly 32 and surgical buttress 24 are placed within a retaining channel 1022 of base 1020 of swaging assembly apparatus 1000. Swaging assembly 1000, or the like, includes a horn 1010 operably connected to a generator (not shown) for mechanically capturing and re-forming the outer edge 36 of cartridge assembly 32. Horn 1010 includes a swage 1012 that may include a curved surface 1014 for forming a rim 40 to retain buttress 24.

In one embodiment, swaging assembly 1000 is operatively mounted on a press assembly (not shown) for approximating horn 1010 towards and away from base 1020. Alternatively, swaging assembly 1000 may be securely mounted relative to base 1020 and base 1020 may be raised and lowered to approximate base 1020 towards and away from horn 1010. The downward pressure exerted on the cartridge assembly 32 by the horn 1010, indicated by the arrow in FIG. 4A, and the shape of swage 1012 displaces the material forming the outer edge 36 of the cartridge assembly 32 over a portion of the tissue contacting surface 38 of the cartridge assembly 32 to entrap the surgical buttress 24 between the formed rim 40 and the tissue contacting surface 38. In embodiments, the addition of heat may cause the outer edge 36 to melt thereby re-shaping the outer edge 36 into a rim 40 over the surgical buttress 24 to retain the surgical buttress 24 on the cartridge assembly 32. It should be understood that the swage 1012 may be configured in a variety of shapes to roll, pinch, wedge, or otherwise re-shape the outer edge 36 of the staple cartridge 32 to capture the outer portion 26 of the surgical buttress 24 to the cartridge assembly 32.

Figure 5:
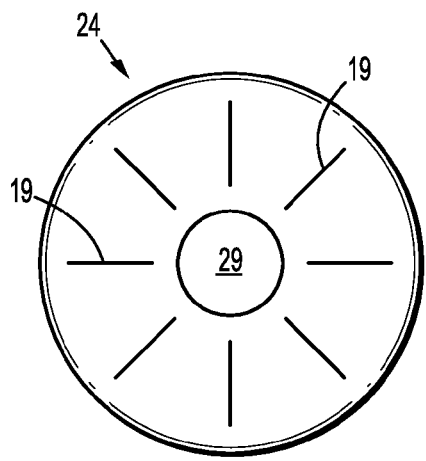
FIG. 5 is a top plan view of a surgical buttress in accordance with another embodiment of the present disclosure.

Alternatively, during manufacture, the swaged outer edge 36 of cartridge assembly 32 may be formed without a surgical buttress 24 present. Instead, a spacing material (not shown) may be placed over the tissue contacting surface 38 of the cartridge assembly 32 to form an inner pocket 42 (FIG. 1C) within which the surgical buttress 24 may be later loaded. After swaging the outer edge 36, the buttress 24 may be wedged between the rim 40 and the tissue contacting surface 38 of the cartridge assembly 32. In embodiments, as illustrated in FIG. 5, the surgical buttress 24 may include slits 19 to facilitate flexible loading and positioning of the surgical buttress 24 under the rim 40 of the cartridge assembly 32.

Referring again to FIGS. 1A-1C, surgical stapling apparatus 10 and detachable anvil assembly 20 are used in an anastomosis procedure to effect joining of intestinal sections 1 and 2, or other body tissue, vessels, or lumens. The anastomosis procedure is typically performed using minimally invasive surgical techniques including laparoscopic means and instrumentation. At the point in the procedure shown in FIG. 1B, a diseased intestinal section has been previously removed, anvil assembly 20 has been applied to the operative site either through a surgical incision or transanally and positioned within intestinal section 2, and tubular body portion 14 of surgical stapling apparatus 10 has been inserted transanally into intestinal section 1. Intestinal sections 1 and 2 are also shown temporarily secured about their respective components (e.g., shaft 23 of anvil assembly 20, and the distal end of tubular body portion 14) by conventional means such as a purse string suture "P".

Thereafter, the clinician maneuvers anvil assembly 20 until the proximal end of shaft 23 is inserted into the distal end of tubular body portion 14 of surgical stapling apparatus 10, wherein a mounting structure within the distal end of tubular body portion 14 engages shaft 23 to effect the mounting. Anvil assembly 20 and tubular body portion 14 are then approximated to approximate intestinal sections 1, 2. Surgical stapling apparatus 10 is then fired. The staples 50 are fired, effecting stapling of intestinal sections 1, 2 to one another. The staples 50 provide enough force to allow the outer portion 26 of the surgical buttress 24 to slip out from within the inner pocket 42 formed between the rim 40 and the tissue contacting surface 38 of the cartridge assembly 32, thereby releasing the surgical buttress 24 from the staple cartridge assembly 32. Alternatively, the buttress slips out from the inner pocket 42 as the surgical stapling apparatus is removed from the tissue. Thereafter, or therewith, knife 30 cuts the portion of tissue and surgical buttress 24 disposed radially inward of the knife 30, to complete the anastomosis.

Figure 6A:
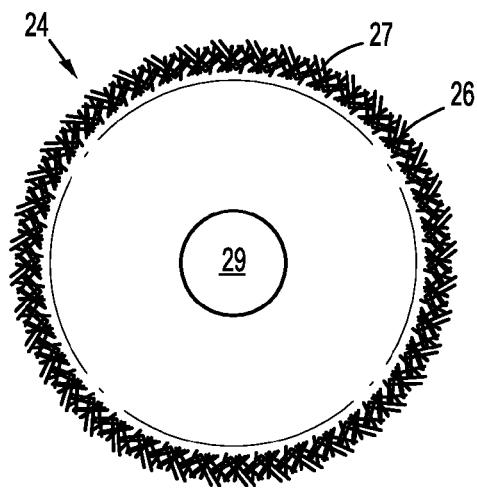
FIG. 6A is a top plan view of a surgical buttress in accordance with yet another embodiment of the present disclosure.
Figure 6B:
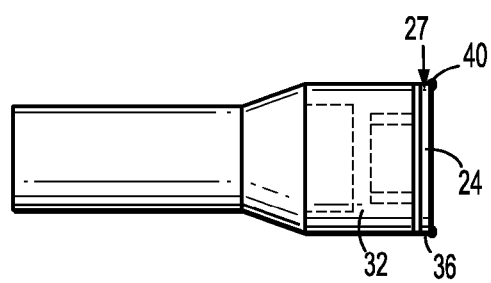
FIG. 6B is a schematic side view of the surgical buttress of FIG. 6A positioned on a staple cartridge assembly in accordance with an embodiment of the present disclosure.

FIGS. 6A and 6B illustrate an embodiment of a surgical buttress 24 including an outer portion 26 having an edge 27 that is frayed, cut, distressed, or otherwise weakened. Frayed edge 27, for example, creates fewer tension points between the surgical buttress 24 and the rim 40 of the cartridge assembly 32 thereby requiring less force to remove the surgical buttress 24 from the cartridge assembly 32 compared to surgical buttresses including an intact outer edge 36, such as those shown in FIGS. 1A and 2, for example. A buttress disclosed in connection with FIGS. 6A and 6B can be used in any of the embodiments disclosed herein.

Figure 7:
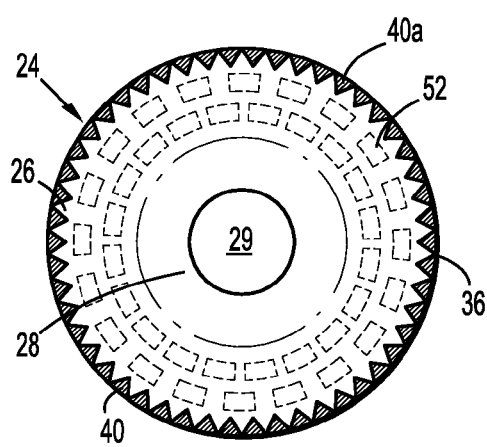
FIG. 7 is a top plan view of a surgical buttress in accordance with an embodiment of the present disclosure illustrating its attachment to a surgical stapling apparatus.

In embodiments, as shown in FIG. 7, release of the surgical buttress 24 may be accomplished by shaping the rim 40 of the cartridge assembly 32 with sharp edges, such as a jagged tooth pattern 40a extending radially inward from the outer edge 36, which will cut the surgical buttress 24, held under tension by staples, as the surgical stapling apparatus is being pulled away after firing. The outer edge 36 of the cartridge assembly 32 maintains a curved or rounded shape to prevent injury during handling and placement within tissue. It is envisioned that other patterns may be formed in the rim 40 of the cartridge assembly 32, as is within the purview of those skilled in the art. A stapling apparatus having a cartridge assembly with sharp edges, as disclosed in connection with FIG. 7 may be used with any of the embodiments disclosed herein.

In other embodiments, a surgical buttress may be retained on the cartridge assembly, or anvil assembly, by encasing at least the outer portion of the surgical buttress with a quick dissolving or rapidly bioerodible polymeric material. Examples of quick dissolving or rapidly bioerodible polymer materials include water soluble polymers such as polyvinyl alcohol, and hydroxylpropyl methylcellulose; biopolymers such as sugars, starches, salts, and gelatin; and derivatives and combinations thereof.

FIG. 8A illustrates a quick dissolving or rapidly bioerodible polymeric material in the form of a film or cap 160 surrounding an outer portion 26 of a surgical buttress 24 and an outer edge 36 of a cartridge assembly 32. Film or cap 160 may be applied to the surgical buttress 24 and cartridge assembly 32 by pressing, snap fitting, dipping, spraying, molding, or other forming processes within the purview of those skilled in the art. In embodiments, the film or cap 160 may dissolve in a sufficient amount of time to allow for placement of the surgical stapling apparatus at the anastomosis site. In other embodiments, the film or cap 160 may split, deform, or have a manual release strip for releasing the surgical buttress 124. In some embodiments, the film or cap 160 may be flexible to allow the surgical buttress 26 to be pulled out from under the film or cap 160. In other embodiments, the film or cap 160 may be rigid and include perforations 162 that will break as the surgical stapling apparatus is being pulled away from the stapled surgical buttress 24 after firing as illustrated in FIG. 8B. It should be understood that a variety of surgical buttress configurations may be utilized with the film or cap 160 of the present disclosure, such as a surgical buttress including slits and/or frayed edges as illustrated in FIGS. 5 and 6A above.

In embodiments, a quick dissolving or rapidly bioerodible polymeric material may encase an entire surgical buttress over a staple cartridge and/or anvil assembly. As illustrated in FIG. 9, for example, a film or cap 260 may be suction fitted, self-molded, or shrink-wrapped around the surgical buttress 24 and a portion of the cartridge assembly 32. Perforations 262 may be provided in film or cap 260, which fracture or split, as the mounting structure within the surgical stapling apparatus is advanced during use. A buttress and/or buttress and stapling apparatus with a quick dissolving or rapidly bioerodible material, as disclosed in connection with FIGS. 8A, 8B, and 9, can be included in any of the embodiments disclosed herein.

Figure 10:
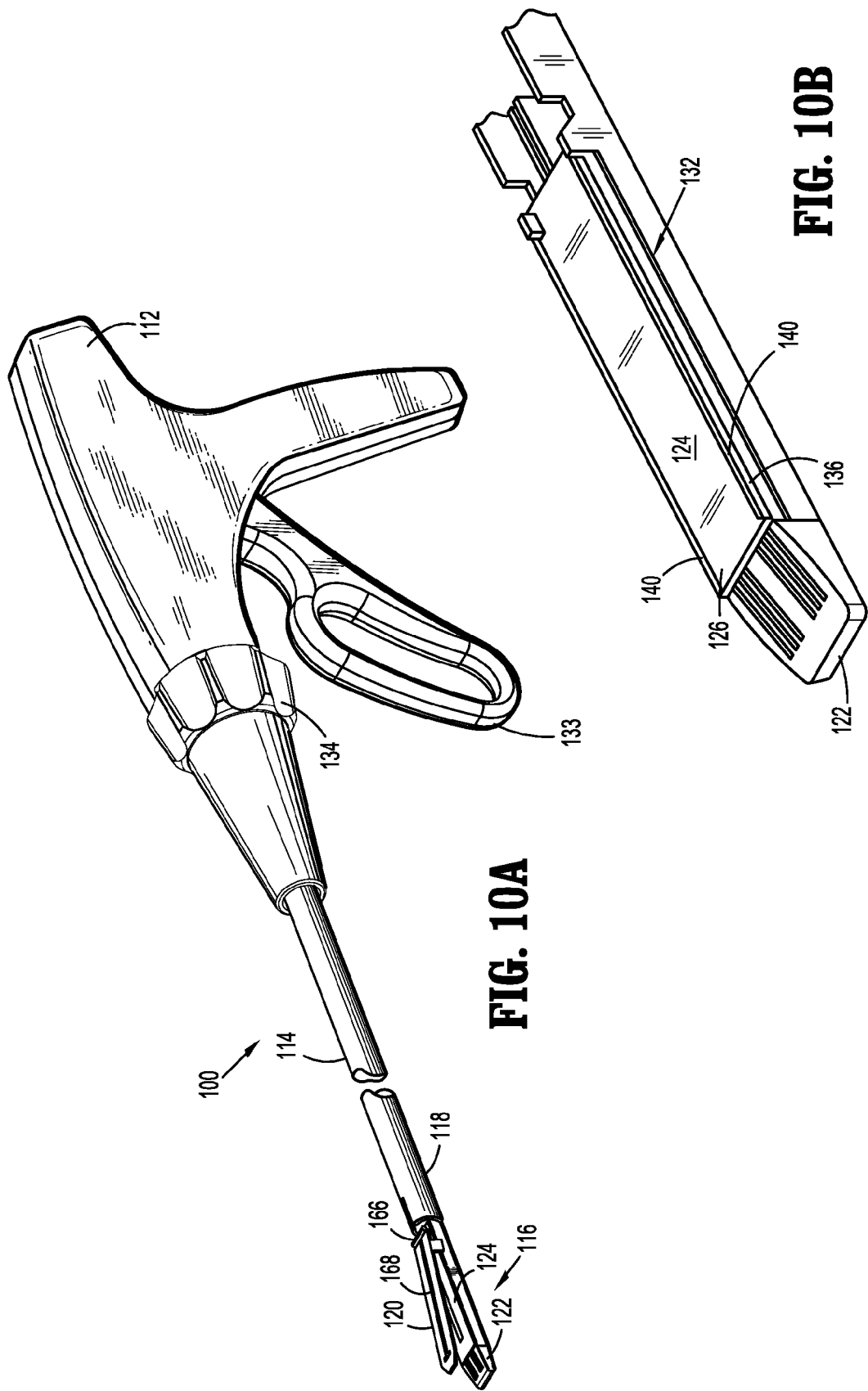
FIG. 10A is a perspective view of an illustrative embodiment of a surgical stapling apparatus in accordance with an embodiment of the present disclosure.
FIG. 10B is a perspective view of the surgical buttress secured to the staple cartridge assembly of the surgical stapling apparatus of FIG. 10A.

Referring now to FIGS. 10A and 10B, an exemplary surgical stapling apparatus or surgical stapler 100 for use in stapling tissue and applying a buttress material or surgical buttress to the tissue. Surgical stapling apparatus 100 generally includes a handle 112 having an elongate tubular member 114 extending distally from handle 112. A jaw assembly 116 is mounted on a distal end 118 of elongate tubular member 114. Jaw assembly 116 includes a staple clinching anvil jaw member 120 and a receiving jaw member 122 configured to receive a staple cartridge assembly 132. Jaw assembly 116 may be permanently affixed to elongate tubular member 114 or may be detachable and thus replaceable with a new jaw assembly 116. Additionally or alternatively, a staple cartridge may be removable and replaceable in the jaw assembly. Staple clinching anvil jaw member 120 is movably mounted on distal end 118 of jaw assembly 116 and is movable between an open position spaced apart from staple cartridge jaw member 122 to a closed position substantially adjacent staple cartridge jaw member 122.

Surgical stapling apparatus 100 further includes a trigger 133 movably mounted on handle 112. Actuation of trigger 133 initially operates to move anvil jaw member 120 from the open to the closed position relative to staple cartridge jaw member 122 and subsequently actuates surgical stapling apparatus 100 to apply lines of staples to tissue. In order to properly orient jaw assembly 116 relative to the tissue to be stapled, surgical stapling apparatus 100 is additionally provided with a rotation knob 134 mounted on handle 112. Rotation of rotation knob 134 relative to handle 112 rotates elongate tubular member 114 and jaw assembly 116 relative to handle 112 so as to properly orient jaw assembly 116 relative to the tissue to be stapled.

A driver 166 is provided to move anvil jaw member 120 between the open and closed positions relative to staple cartridge jaw member 122. Driver 166 moves between a longitudinal slot 168 formed in anvil jaw member 120. A knife (not shown) is associated with driver 166 to cut tissue captured between anvil jaw member 120 and staple cartridge jaw member 122 as driver 166 passes through slot 168.

As illustrated in the current embodiment and shown in FIG. 10B, a surgical buttress 124 is releasably attached to the staple cartridge assembly 132 and/or the anvil jaw member 120 by an outer edge 136 of the cartridge assembly 132. The outer edge 136 may be swaged, molded or otherwise formed. Swaged outer edge 136, for example, forms a rim 140 overlying tissue contacting surface 138 of cartridge assembly 132 for capturing an outer portion 126 of surgical buttress 124, in a manner similar to that of swaged outer edge 36, as described above, and may be formed as discussed above. While the rim 140 is illustrated in the present embodiment as being discontinuous and extending along two sides of the surgical buttress 124, it is envisioned that the rim 140 may continuously extend around the surgical buttress or include a plurality of tabs surrounding the surgical buttress similar to the embodiment of FIG. 2.

Figure 11:
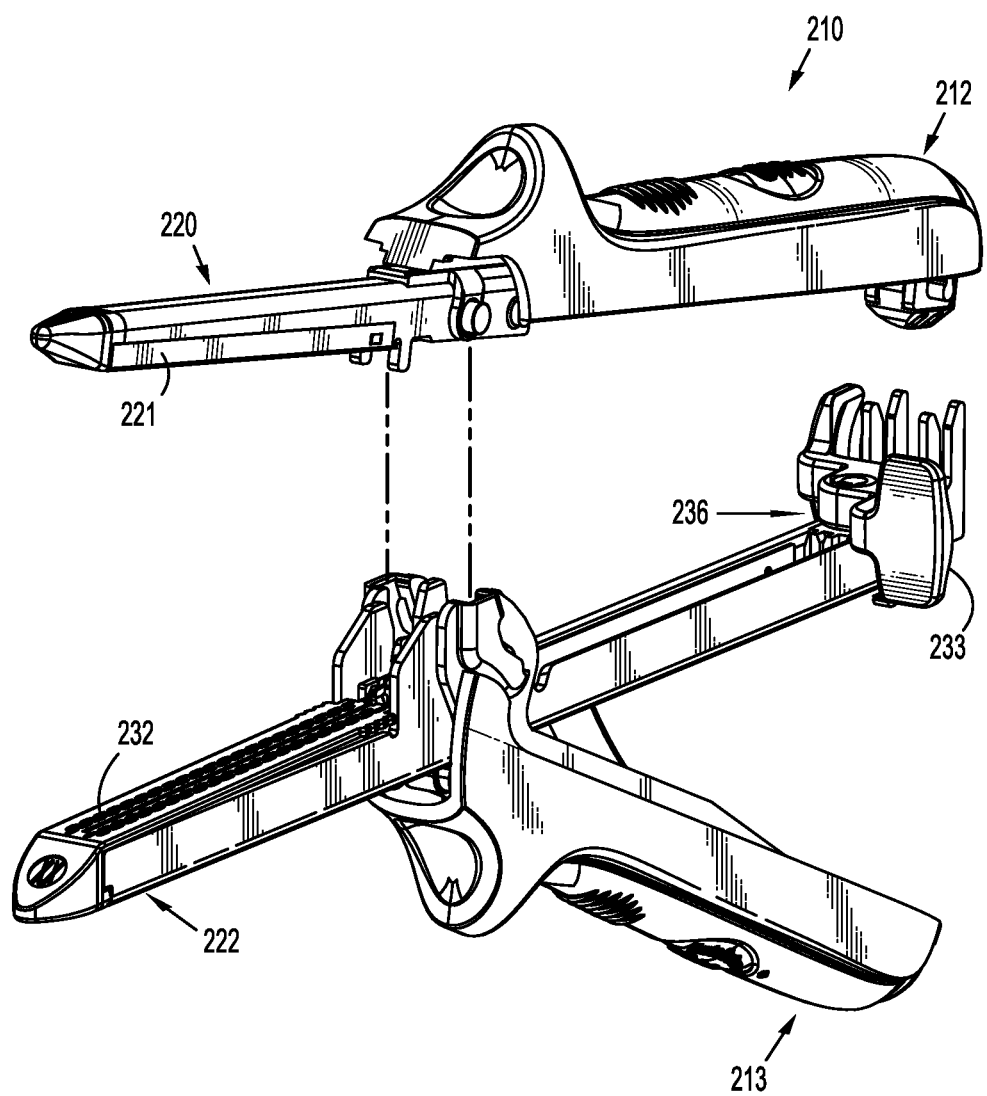
FIG. 11 is a perspective view of another illustrative embodiment of a surgical stapling apparatus for use with a surgical buttress of the present disclosure.

The surgical buttress of the present disclosure, in particular surgical buttress 124, may also be adapted for use with a surgical stapling apparatus, such as that shown and described in U.S. Pat. No. 7,334,717, entitled "Surgical Fastener Applying Apparatus," the entire content of which is incorporated herein by reference. As illustrated in FIG. 11, surgical stapling apparatus 210 includes an anvil receiving section 220 and a cartridge receiving section 222. A surgical buttress (not shown) may be attached to at least one of an anvil 221 coupled to the anvil receiving section 220, a staple cartridge assembly 232 coupled to the cartridge receiving section 222, or both, as discussed above, by a swaged outer edge. The anvil receiving section 220 and the cartridge receiving section 222 are pivotally connected via handles 212, 213 for approximation during use. Following approximation of the anvil receiving section 220 and the cartridge receiving section 222, the surgical stapling apparatus 210 is fired by driving a firing slide 236 distally through the advancement of a firing lever 233. Distal movement of the firing slide 236 causes a plurality of cam bars to engage camming surfaces that interact with a plurality of pushers to expel a plurality of surgical staples (not shown) from the cartridge receiving section 222. The staples are positioned on either side of a track which guides a knife (not shown) during longitudinal movement. The knife severs tissue along a cut-line. Fastening of the staples through the surgical buttress retains the surgical buttress within tissue and provides a force that allows the surgical buttress to slip out of the swaged outer edge of the cartridge assembly as the surgical stapling apparatus is pulled away from the tissue, thereby releasing the surgical buttress from the staple cartridge.

Figure 12:
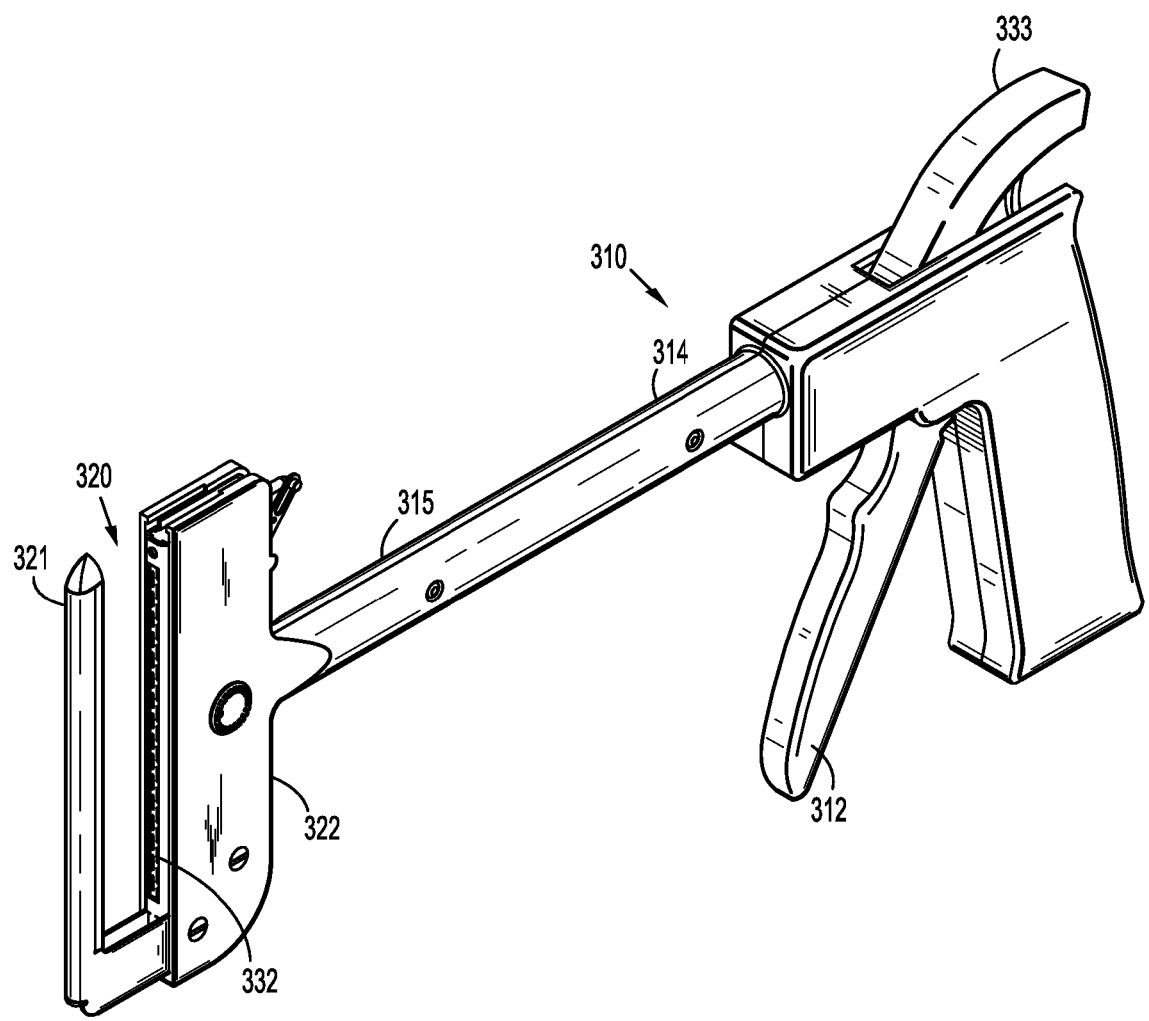
FIG. 12 is a perspective view of yet another illustrative embodiment of a surgical stapling apparatus for use with a surgical buttress of the present disclosure.

The surgical buttress of the present disclosure, in particular surgical buttress 124, may also be adapted for use with a transverse surgical stapling apparatus 310, as illustrated in FIG. 12. An exemplary transverse surgical stapling apparatus is shown and described in U.S. Pat. No. 5,964,394, entitled "Surgical Fastener Applying Device," the entire content of which is incorporated herein by reference. The surgical stapling apparatus 310 includes an approximation lever 333, a movable handle 312, an elongated portion 314 that extends distally from the handle 312, and an arm 322 that extends from a distal end 315 of the elongated portion 314. The surgical stapling apparatus 310 further includes an anvil 321 that is orthogonally affixed to the arm 322, and a cartridge receiver 320 that is operatively coupled to the distal end 315 of the elongated portion 314 for retention of a staple cartridge assembly 332. One or more pushers are moved through the cartridge assembly to drive staples against the anvil simultaneously or sequentially. A surgical buttress (not shown) may be joined to at least one of the anvil 321, staple cartridge assembly 332, or both as discussed above, via a swaged outer edge.

In embodiments, at least one bioactive agent may be combined with any of the surgical buttresses of the present disclosure. The at least one bioactive agent may be disposed on a surface of the surgical buttress and/or impregnated therein. In these embodiments, the surgical buttress can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the surgical buttress in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Other bioactive agents which may be included as a bioactive agent in the surgical buttress of the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

In embodiments, a reinforcement member may be positioned within or over any of the surgical buttresses disclosed herein. In embodiments utilizing a multilayered surgical buttress, one or more reinforcement members may be positioned between, within, or at an external surface of a layer of the surgical buttress as are disclosed, for example, in U.S. Patent Application Publication No. 2009/0001122, reference above, the disclosure of which is hereby incorporated by reference herein.

Further aspects of the present disclosure are described in the following numbered paragraphs.

1. A surgical stapling apparatus including a releasable buttress material, the surgical stapling apparatus comprising: a cartridge assembly including a plurality of staples and a tissue contacting surface defining staple retaining slots; an anvil assembly including a tissue contacting surface defining staple pockets for forming staples expelled from the staple retaining slots of the cartridge assembly; a knife disposed within a knife slot formed in the tissue contacting surface of the cartridge assembly; wherein one of the cartridge assembly and the anvil assembly includes a rim defining an inner pocket; and a buttress material including an outer portion disposed in the inner pocket of the one of the cartridge assembly and the anvil assembly.

2. The surgical stapling apparatus of paragraph 1, wherein the outer edge of the one of the cartridge assembly and the anvil assembly is swaged to form the rim.

3. The surgical stapling apparatus of any preceding paragraph, wherein the rim continuously extends around an entire perimeter of the buttress material.

4. The surgical stapling apparatus of any preceding paragraph, wherein the rim includes a plurality of discontinuous tabs extending around the buttress material.

5. The surgical stapling apparatus of any preceding paragraph, wherein the rim includes sharp edges extending radially inward of the outer edge.

6. The surgical stapling apparatus of any preceding paragraph, wherein the buttress material includes slits.

7. The surgical stapling apparatus of any preceding paragraph, wherein the outer portion of the buttress material is frayed.

8. The surgical stapling apparatus of any preceding paragraph, wherein the rim includes a first rim on the anvil assembly and a second rim on the cartridge assembly.

9. The surgical stapling apparatus of paragraph 8, wherein the buttress material of the anvil assembly is different from the buttress material of the cartridge assembly.

10. The surgical stapling apparatus of any preceding paragraph, wherein the cartridge assembly is associated with a body portion of the surgical stapling apparatus and the anvil assembly includes a shaft removably mountable to the body portion, the anvil assembly being movable toward and away from the body portion.

11. The surgical stapling apparatus of paragraph 10, wherein the cartridge assembly and the anvil assembly are circular, and wherein the buttress material includes a central opening dimensioned to receive the shaft of the anvil assembly.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Accordingly, the subject matter of the present disclosure is not to be limited by what has been particularly shown and described, except as indicated by the appended claims.

What is claimed is:

1. A surgical stapling apparatus including a releasable buttress material, the surgical stapling apparatus comprising:
    a cartridge assembly including a plurality of staples and a tissue contacting surface defining staple retaining slots, the cartridge assembly including a swaged outer edge having a rim overlapping the tissue contacting surface of the cartridge assembly in spaced relation therewith and defining an inner pocket between the tissue contacting surface and the rim, the rim including an annular array of teeth extending radially inward of the swaged outer edge;
    an anvil assembly including a tissue contacting surface defining staple pockets for forming staples expelled from the staple retaining slots of the cartridge assembly; and
    a buttress material including an outer portion retained within the swaged outer edge of the cartridge assembly.

2. The surgical stapling apparatus of claim 1, wherein the rim continuously extends around an entire perimeter of the buttress material.

3. The surgical stapling apparatus of claim 1, wherein the rim includes a plurality of discontinuous tabs extending around the buttress material.

4. The surgical stapling apparatus of claim 1, wherein the annular array of teeth define sharp edges.

5. The surgical stapling apparatus of claim 1, wherein the buttress material includes slits.

6. The surgical stapling apparatus of claim 1, wherein the outer portion of the buttress material is frayed.

7. The surgical stapling apparatus of claim 1, wherein the anvil assembly includes a swaged outer edge and a buttress material retained within the swaged outer edge of the anvil assembly.

8. The surgical stapling apparatus of claim 7, wherein the swaged outer edge of the anvil assembly includes a rim overlapping the tissue contacting surface of the anvil assembly in spaced relation therewith and defines an inner pocket between the tissue contacting surface and the rim.

9. The surgical stapling apparatus of claim 7, wherein the buttress material retained within the swaged outer edge of the anvil assembly includes slits.

10. The surgical stapling apparatus of claim 7, wherein the outer portion of the buttress material retained within the swaged outer edge of the anvil assembly is frayed.

11. The surgical stapling apparatus of claim 7, wherein the buttress material of the anvil assembly is different from the buttress material of the cartridge assembly.

12. The surgical stapling apparatus of claim 1, wherein the cartridge assembly is associated with a body portion of the surgical stapling apparatus and the anvil assembly includes a shaft removably mountable to the body portion, the anvil assembly being movable toward and away from the body portion.

13. The surgical stapling apparatus of claim 12, wherein the cartridge assembly and the anvil assembly are circular, and wherein the buttress material includes a central opening dimensioned to receive the shaft of the anvil assembly.

14. The surgical stapling apparatus of claim 1, wherein the cartridge assembly is associated with a first jaw and the anvil assembly is associated with a second jaw, the first and second jaws being selectively movable relative to one another from a first spaced apart position to a second position wherein the first and second jaws cooperate to grasp tissue therebetween.

* * * * *